United States Patent [19]
Gross et al.

[11] Patent Number: 5,866,546
[45] Date of Patent: Feb. 2, 1999

[54] TREATMENT FOR DIABETES

[75] Inventors: David Gross, Mevasseret-Zion; Lola Weiss; Shimon Slavin, both of Jerusalem, all of Israel; Hiroshi Okamoto, Miyagi, Japan

[73] Assignee: Hadasit Medical Research Services and Development Company Ltd.

[21] Appl. No.: 844,518

[22] Filed: Apr. 18, 1997

[51] Int. Cl.[6] ............................ A61K 31/47; A61K 38/00
[52] U.S. Cl. .................. 514/21; 514/2; 514/311; 514/866
[58] Field of Search .................. 514/2, 21, 311, 514/866

[56] References Cited

U.S. PATENT DOCUMENTS 5,344,832  9/1994  Cincotta et al. .................. 514/288

FOREIGN PATENT DOCUMENTS

303233 A2  2/1989  Japan .

OTHER PUBLICATIONS

Chemical Abstracts vol. 111: 128263r Okamoto et. al., 1989.
Chemical Abstracts vol. 121: 107153w Orwoll et. al., 1994.
Chemical Abstracts vol. 122: 177926v Gross et. al., 1995.
Chemical Abstracts vol. 122: 256070q Reddy et. al., 1995.

*Primary Examiner*—Leonard Schenkman
*Attorney, Agent, or Firm*—Mark M. Friedman

[57] ABSTRACT

A composition for the treatment of diabetes and a method of use thereof. The composition includes an immunoregulator, preferably Linomide, and a β cell proliferative agent, preferably reg protein. The composition has been shown to be effective in both inhibiting the progression of diabetes, and reversing the course of the disease, in the NOD mouse model.

3 Claims, 2 Drawing Sheets

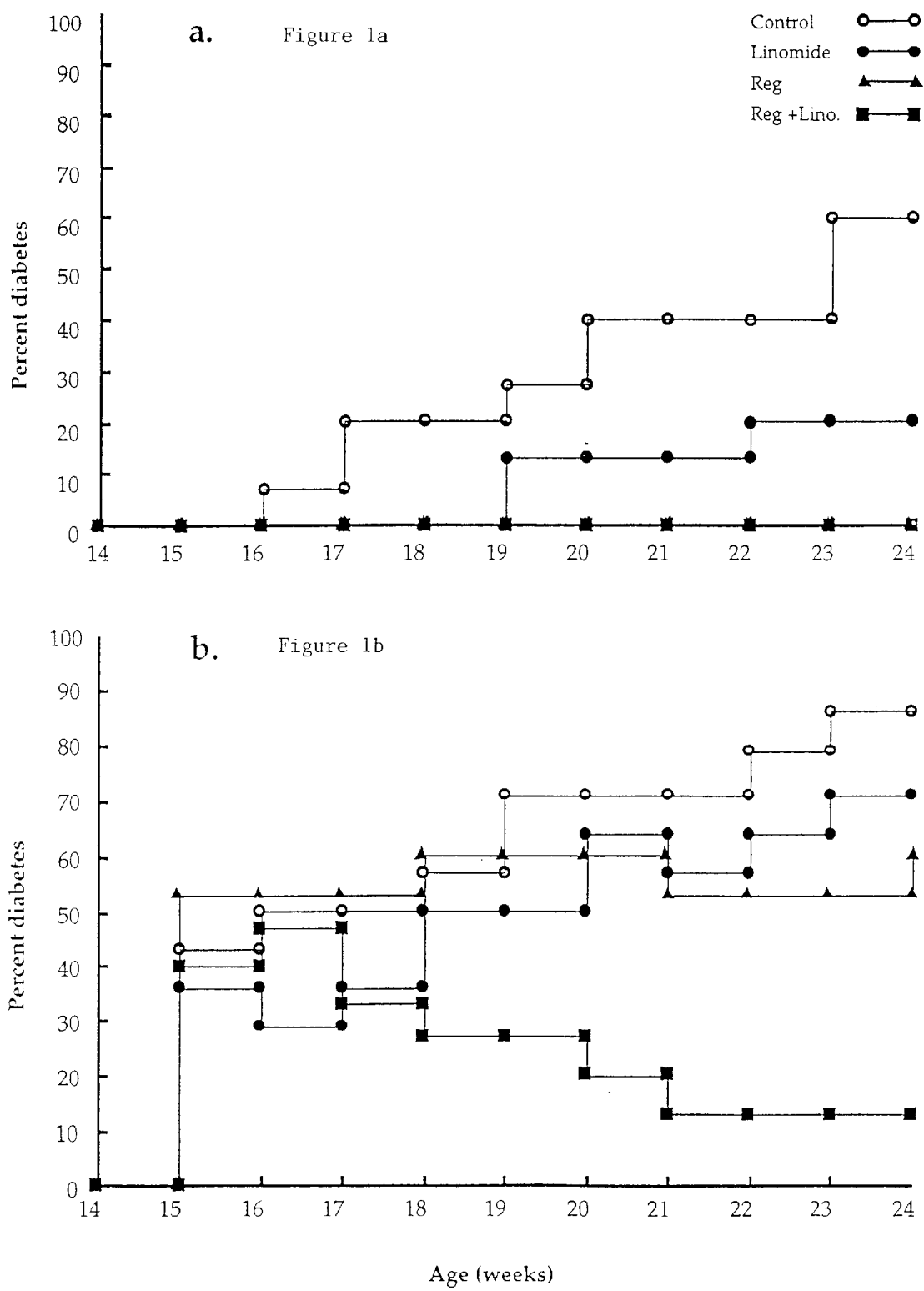

TREATMENT FOR DIABETES

FIELD AND BACKGROUND OF THE INVENTION

The present invention relates to a treatment for diabetes which combines an immunoregulator and a β cell proliferation agent and, in particular, which includes both Linomide and the reg protein.

Diabetes mellitus is particularly characterized by hyperglycemia, although other related clinical manifestations include vascular complications and altered metabolism of lipids, proteins and carbohydrates. For example, the altered metabolism of lipids can lead to increased production of ketones, potentially leading to ketonemia and acidosis. Vascular changes which occur include the thickening of the capillary basement membrane, leading to narrowing of the lumen of blood vessels and reduced blood circulation. Such reduced circulation can, in turn, cause retinopathy, neuropathy and gangrene of the extremities. Thus, diabetes mellitus has consequences which extend far beyond hyperglycemia.

Diabetes mellitus can be divided into two clinical syndromes, Type I and Type II diabetes mellitus. Type I, or insulin-dependent diabetes mellitus (IDDM), is a chronic autoimmune disease characterized by the extensive loss of β cells in the pancreatic Islets of Langerhans (hereinafter referred to as "islets"), which produce insulin. As these cells are progressively destroyed, the amount of secreted insulin decreases, eventually leading to hyperglycemia (abnormally high level of glucose in the blood) when the amount secreted drops below the level required for euglycemia (normal blood glucose level). Although the exact trigger for this immune response is not known, patients with IDDM have high levels of antibodies against pancreatic β cells. However, not all patients with high levels of these antibodies develop IDDM.

One possible explanation for this apparent discrepancy is the capacity of the pancreas to expand β cell mass through proliferation of these cells. For example, at the onset of IDDM, the pancreas has been shown to be capable of neoformation of islets [W. Gepts and P. M. Lecompte, *Am. J Med.*, 70:105–115, 1981]. β cell proliferation and regeneration has also been demonstrated in animal models of diabetes with reduced β cell mass, and in transgenic mice with β cell damage [S. Bonner-Weir et al., *Diabetes*, 42:1715–1720, 1993; D. Gu and N. Sarvetnick, *Development*, 118:33–46, 1993]. Unfortunately, the lack of significant proliferative ability of mature β cells is a major impediment to the treatment of diabetes, particularly due to the relatively late diagnosis of the disease.

Patients with IDDM are usually diagnosed when clinical symptoms are manifested, such as hyperglycemia. However, by the time such symptoms are apparent, the disease has been progressing over an extensive period of time and extensive loss of pancreatic β cells has occurred. Therefore, treatments such as immunoregulators, which seek to inhibit the autoimmune response, can only arrest further progress of IDDM and cannot reverse the extensive pancreatic cell loss. Unless the lost β cells are replaced, the patient will continue to experience clinical symptoms of IDDM, even as the course of the disease itself is halted. Thus, a successful treatment for IDDM must both halt the further progression of the disease and induce the replacement of lost pancreatic β cells.

There is therefore an unmet medical need for a treatment for diabetes which both halts the further progress of the disease and which ameliorates or reverses clinical symptoms by inducing the proliferation of pancreatic β cells.

SUMMARY OF THE INVENTION

According to the teachings of the present invention, there is provided a composition for the treatment of diabetes, including: (a) an immunoregulator; and (b) a β cell proliferative agent. Preferably, the immunoregulator is Linomide. Also preferably, the β cell proliferative agent is reg protein. Most preferably, a pharmaceutically acceptable carrier is included.

According to other embodiments of the present invention, there is provided a method for treating diabetes in a subject, including the step of administering an effective amount of a composition to the subject, the composition including an immunoregulator and a β cell proliferative agent in a pharmaceutically acceptable carrier. Preferably, the immunoregulator is Linomide. Also preferably, the β cell proliferative agent is reg protein.

Hereinafter, the term "subject" refers to the human or lower animal to whom the composition of the present invention was administered. Hereinafter, the terms "diabetes", "diabetes mellitus", "Type I diabetes" and "IDDM" all refer to insulin-dependent diabetes mellitus. Hereinafter, "Linomide" is defined as quinoline-3-carboxamide, and pharmaceutically acceptable salts and bioequivalents thereof (Pharmacia Upjohn, Lund, Sweden). The terms "reg" and "reg protein" include those sequences given as Swiss Prot Accession No. P05451, and EMBL Accession No. M18963, sequences disclosed or identified in PCT Application No. WO 94/12203, European Application No. EP 383453, European Application No. EP 303233 and European Application No. EP 286114, as well as pharmaceutically active mutants, variants or portions thereof, and combinations of these sequences and pharmaceutically active mutants, variants or portions thereof.

Hereinafter, the term "immunoregulator" is defined as a substance which substantially prevents, reduces or inhibits the autoimmune reaction seen in insulin-dependent diabetes mellitus. A preferred example of such an immunoregulator is Linomide, although other examples include insulin, vitamin D, nicotinamide, corticosteroids and pharmaceutically acceptable salts or equivalents thereof. The term "β cell proliferative agent" is defined as a substance which substantially induces the proliferation of β cells in the pancreas. A preferred example of such a β cell proliferative agent is the reg protein, although other examples include growth hormone and prolactin, and pharmaceutically acceptable mutants, variants and portions thereof. Hereinafter, the term "NOD mouse" is defined as a non-obese diabetic mouse. These mice are commercially available (Jackson Laboratories, Bar Harbor, Me., USA). Hereinafter, the term "treat" includes substantially inhibiting, slowing or reversing the progression of a disease, substantially ameliorating clinical symptoms of a disease or substantially preventing the appearance of clinical symptoms of a disease.

BRIEF DESCRIPTION OF THE DRAWINGS

The invention is herein described, by way of example only, with reference to the accompanying drawings, wherein:

FIGS. 1A and 1B show the ability of the composition of the present invention to substantially reverse the course of diabetes in NOD mice.

DESCRIPTION OF THE PREFERRED EMBODIMENTS

Figure 2A:
FIGS. 2A–2F demonstrate β cell proliferation in NOD mice treated with the composition of the present invention.
Figure 2B:
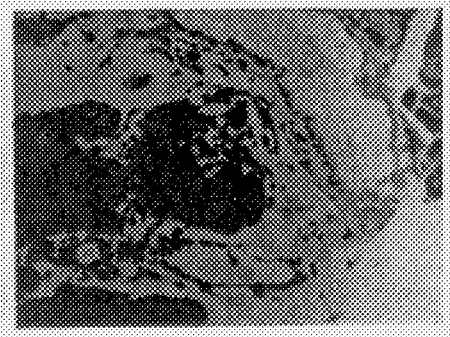

The present invention is a treatment for diabetes mellitus, and in particular for insulin-dependent diabetes mellitus (IDDM), which combines an immunoregulator and a β cell proliferative agent. As demonstrated below, such a combination is particularly efficacious not only to substantially slow or halt the progression of IDDM, but even to substantially reduce or reverse the clinical manifestations of the disease.

Although the present invention is not limited to this single combination, the immunoregulator tested was Linomide, while the β cell proliferative agent was reg protein. Such a combination was neither taught nor suggested in the prior art, although each of these substances had been examined separately in prior art references.

Linomide, the immunoregulator, was shown to prevent diabetes from developing in NOD mice if administered sufficiently early, before clinical symptoms have developed [D. J. Gross et al., *Diabetologia*, 37:1195–1201, 1994]. However, once clinical symptoms have appeared in these mice, Linomide was shown to only partially ameliorate the disease. Unfortunately, as noted above, human patients often are diagnosed only at such a relatively late stage of the disease, so that Linomide alone would not be effective as a treatment for patients with IDDM. In order to overcome the depletion of β cell mass seen in NOD mice with clinical symptoms of diabetes, prior art studies indicated that transplantation of islet cells followed by immunoregulation with Linomide were required [S. Slavin et al., *Cell Transplantation*, 5:627–630, 1996]. However, such transplantations would be difficult to perform in human patients for a number of reasons. First, sufficient donor material must be located, which is generally a problem for human transplantation. Second, extensive drug treatment is required to prevent rejection of the transplanted tissue. Finally, transplantation itself is a complicated, difficult medical procedure. Thus, other treatments for patients with IDDM are required.

Reg protein, the β cell proliferative agent used in the composition of the present invention, is a C-type lectin originally cloned from a cDNA library prepared from regenerating islets, hence its name [K. Terazono et al., *J Biol. Chem.*, 263:2111–2114, 1988]. Reg expression has been demonstrated at the protein and mRNA levels in replicating islets, as well as in the Syrian golden hamster and rat islet regeneration models [K. Terazono et al., *Diabetologia*, 33:250–252, 1990; R. Rafaeloff et al., *Diabetologia*, 38:906–913, 1995; and M. E. Zenilman et al., *Surgery*, 119:576–584, 1996]. However, other studies have failed to demonstrate reg expression in pancreatic islets or β cell lines [C. Miyaura et al., *Mol. Endocrinol.*, 5:226–234, 1991; and F. E. Smith et al., *Diabetologia*, 37:994–999, 1994]. Thus, the exact role of reg is unclear from the prior art teachings.

In one study, reg protein was found to ameliorate diabetes in rats resulting from removal of the pancreas [T. Watanabe et al., *PNAS*, 91:3589–3592, 1994]. However, against the teachings of this prior art reference, reg protein alone was not found to be effective in inhibiting or reversing the progression of diabetes, as shown in Examples 1 and 2 below. Thus, the prior art only taught the efficacy of reg protein alone, while the results shown below not only teach against the prior art, but also demonstrate the efficacy of the combination of Linomide and reg protein. Such a combination was neither taught nor suggested in the prior art.

The principles of a treatment for diabetes according to the present invention may be better understood with reference to the Examples, drawings and the accompanying description.

EXAMPLE 1

Occurrence of Diabetes in NOD Mice

Female NOD (non-obese diabetic) mice are characterized by displaying IDDM with a course which is similar to that found in humans, although the disease is more pronounced in female than male NOD mice. Hereinafter, unless otherwise stated, the term "NOD mouse" refers to a female NOD mouse. NOD mice have a progressive destruction of β cells which is caused by a chronic autoimmune disease. Thus, NOD mice begin life with euglycemia, or normal blood glucose levels. By about 15 to 16 weeks of age, however, NOD mice start becoming hyperglycemic, indicating the destruction of the majority of their pancreatic β cells and the corresponding inability of the pancreas to produce sufficient insulin. Thus, both the cause and the progression of the disease are similar to human IDDM patients.

For the experiments performed in both this Example and Example 2, female NOD mice were used. These mice were either untreated (control), treated with Linomide alone, reg alone or a combination of reg and Linomide. The effect of these various treatments on the progression of diabetes was measured. As shown in FIGS. 1A and 1B, only the combination of reg and Linomide was able to substantially halt and even reverse the course of diabetes in glucose intolerant mice. The experimental method was as follows.

At 14 weeks of age, the female NOD mice were phenotyped according to glucose tolerance. Glucose tolerance was measured with the intraperitoneal glucose tolerance test (IPGTT). Briefly, blood was drawn from the paraorbital plexus at 0 minutes and 60 minutes after the intraperitoneal injection of glucose (1 g/kg body weight). Normal tolerance was defined as plasma glucose at 0 minutes of less than 144 mg %, or at 60 minutes of less than 160 mg %. Blood glucose levels were determined with a Glucometer Elite apparatus.

Based upon this phenotypic analysis, animals were allocated to the different experimental groups. In particular, animals with more elevated blood glucose levels were assigned to the impaired glucose tolerance group. The mice were fed ad libitum and were supplied with acidified water (pH 2.3).

The glucose tolerant and intolerant mice were further subdivided into control, Linomide, reg and Linomide/reg combination groups. Mice in the control group received an interperitoneal injection of vehicle daily, six times per week. Mice in the Linomide group received 0.5 mg/ml of Linomide in normal, non-acidified drinking water on a daily basis. Mice in the reg group received an interperitoneal injection of reg protein in vehicle daily, six times per week. Mice in the Linomide/reg combination group received both Linomide and reg as described above.

The reg protein was prepared as follows. The human reg cDNA encompassing the coding sequence was introduced into a *Pichia pastoris* expression vector for production of recombinant human reg protein [K. A. Barr et al., *Pharm. Eng.*, 12:48–51, 1992]. Yeast supernatant, containing reg protein, was concentrated by precipitation with 60% saturated solution of ammonium sulfate. The precipitate was dissolved and then further concentrated and desalted using an Intersep apparatus (Intersep filtration systems, Berkshire, UK) with a 10 kDa cut-off membrane. The resultant reg protein migrated on SDS-PAGE to the same position as the recombinant reg protein in unprocessed yeast medium and after ion-exchange chromatography, showing a double-band at 16.5 kDa. Furthermore, the resultant protein was also detected by a human reg anti-serum on a western blot. Prior to injection, the lyophilized protein was reconstituted at a concentration of 1 mg/ml in 50 mM acetic acid.

The level of urine glucose in the NOD mice was determined on a bi-weekly basis using Labstix (Bayer Diagnostics, Hampshire, England). Weight and fluid intake were also determined on a bi-weekly basis. The onset of diabetes was defined after the appearance of glucosuria on two consecutive determinations. After 10 weeks of treatment, an additional IPGTT was performed and animals were sacrificed the following day. Results are shown in FIGS. 1A and 1B, as well as in Table 1.

Over the 10 week course of treatment, control animals in both the glucose tolerant (FIG. 1A) and glucose intolerant (FIG. 1B) developed diabetes at a rate of 60% and 86%, respectively. Thus, high rates of diabetes occur even in NOD mice which were initially glucose tolerant if no intervention is made.

Linomide alone was able to prevent the development of diabetes in glucose tolerant animals, as shown in FIG. 1A. This result is expected, since Linomide inhibits the autoimmune response which causes diabetes in NOD mice. Since these animals were still euglycemic at the onset of treatment, Linomide was effective in preventing progression of the disease. However, Linomide alone was not able to inhibit or reverse progression of diabetes in glucose intolerant mice, since these mice had presumably already suffered significant β cell loss at the onset of treatment, so inhibition of further progression would not prevent diabetes in these animals.

The reg protein alone conferred only partial protection for glucose tolerant mice, as shown in FIG. 1A. Only 20% of glucose tolerant mice developed diabetes when treated with reg protein, while 60% of glucose tolerant mice in the control group developed diabetes. However, as shown in FIG. 1B, the reg protein alone did not inhibit or reverse the course of diabetes in glucose intolerant mice, possibly because the autoimmune disease process was not affected by the reg protein. Thus, although the reg protein promotes β cell proliferation as shown in Example 2, these cells continued to be destroyed by the autoimmune reaction and so the development of diabetes was not affected in these mice.

The combination of Linomide and reg protein completely prevented the development of diabetes in glucose tolerant mice, as shown in FIG. 1A. However, it should be noted that Linomide alone was also able to prevent the development of diabetes in these mice. Thus, the inhibition of the immune process was clearly the deciding factor in the protection of the glucose tolerant mice.

Glucose intolerant mice, by contrast, initially rapidly developed diabetes even when treated with the combination of Linomide and reg protein, as shown in FIG. 1B. After the first 2 weeks of treatment, the incidence of diabetes was 30–50% in all glucose intolerant mice. However, the incidence of diabetes actually decreased after 4 weeks of treatment with the combination of reg and Linomide. By the end of the treatment period, only 13% of mice given the combination of reg and Linomide had diabetes, as compared to 80% of mice in the control group (p<0.0001). Thus, the combination of Linomide and reg protein actually reversed the course of the disease in glucose intolerant NOD mice, rather than merely inhibiting its further progression.

This result is confirmed by the measurement of blood glucose levels in NOD mice, before and after treatment. Blood glucose levels were measured as described above in both glucose tolerant and intolerant mice in all four groups. Results are shown in Table 1. The numbers in parentheses indicate the number of mice tested in each group.

TABLE 1

Blood Glucose Measurements

| Group: Age | Glucose Tolerant | | Glucose Intolerant | |
|---|---|---|---|---|
| (weeks) | 14 | 24 | 14 | 24 |
| Control | 6.5 ± 0.2 (15) | 15.4 ± 2.7 (15) | 8.2 ± 0.5 (14) | 21.5 ± 3.1 (9) |
| reg alone | 6.7 ± 0.2 (15) | 9.2 ± 1.9 (13) | 8.2 ± 0.4 (14) | 19.1 ± 3.4 (13) |
| Linomide | 6.4 ± 0.2 (16) | 7.3 ± 0.5 (16) | 7.8 ± 0.5 (15) | 20.9 ± 2.9 (13) |
| reg + Linomide | 6.5 ± 0.2 (17) | 7.8 ± 0.9 (12) | 8.4 ± 0.4 (16) | 8.9 ± 0.6 (9) |

As can be seen from Table 1, NOD mice in the control group which were initially glucose tolerant had high blood glucose levels and had become glucose intolerant by the end of the treatment period. However, initially glucose tolerant mice in all three treatment groups, Linomide alone, reg alone and Linomide+reg, maintained blood glucose levels similar to those seen before the start of treatment. Thus, all three treatments effectively prevented the development of high blood glucose levels in initially glucose tolerant mice.

Mice which were initially glucose intolerant started with higher blood glucose levels before treatment and developed significantly higher blood glucose levels by the end of treatment in all groups except for the group treated with the combination of reg and Linomide (p<0.0005). Thus, only the combination of reg and Linomide was able to prevent the development of higher blood glucose levels in initially glucose intolerant mice.

IPGTT determinations were also performed as described above, both before and after treatment, in reg-treated glucose intolerant mice, as shown in Table 2. Mice began treatment at age 14 weeks and ended it 10 weeks later, at age 24 weeks. Blood glucose was measured at the start of the IPGTT determination (0 minutes) and at the end (60 minutes).

TABLE 2

IPGTT in Glucose Intolerant Mice

| | Blood Glucose (mmol/L) | |
|---|---|---|
| Age (weeks) | 0 minutes | 60 minutes |
| 14 | 8.2 ± 2 | 15.3 ± 6.2 |
| 24 | 7.9 ± 2.7 | 10.2 ± 2.4 |

Reg treatment prevented the deterioration of glucose tolerance in 6 of 10 mice which did not develop frank diabetes by the end of the treatment period. By contrast, all mice succumbed to diabetes in the control group. Linomide treatment alone also did not prevent the deterioration of glucose tolerance (results not shown). Thus, only reg treatment enabled initially glucose intolerant mice to maintain relatively stable responses to the IPGTT.

EXAMPLE 2

Histological Examination of NOD Mice

Histological examination of tissue samples from NOD mice demonstrated the ability of the composition of the present invention, a combination of an immunoregulator and a β cell proliferation agent, to increase the relative concentration of β cells in the pancreas, as shown in FIGS. 2A–2F. Such stimulation was not seen in NOD mice treated with either Linomide or reg protein alone. The experimental method was as follows.

The mice from Example 1 were sacrificed at the end of the treatment period and tissue samples were taken from the pancreas. The samples were fixed in 10% formalin in 0.9% saline and embedded in wax. Two sets of 5 serial 5 µm sections were cut for immunolabelling at a cutting interval of 150 µm. Sections were immunolabelled for insulin (guinea pig anti-insulin antisera dilution 1:1000, ICN Thames U.K.) and glucagon (rabbit anti-pancreatic glucagon antisera dilution 1:2000) and detected with peroxidase conjugated anti-guinea pig (Dako, High Wycombe, U.K.) or peroxidase conjugated anti-rabbit antisera (dilution 1:50, Dako). Specific histological samples are shown in FIGS. 2A–2F, and overall proportions of β cells for glucose tolerant mice are given in Table 3.

Glucose intolerant mice in the control (FIG. 2A) or Linomide-treated (FIG. 2B) group had small islets consisting largely of glucagon cells with no discernible β cells. Small numbers of β cells were observed in one animal from the reg protein-treated group and in one animal from the group treated with the combination of Linomide and the reg protein (data not shown). Thus, the composition of the present invention did not have as strong an effect on the visible mass of β cells as it did on the clinical manifestations of diabetes in glucose intolerant animals.

Figure 2C:
Figure 2D:
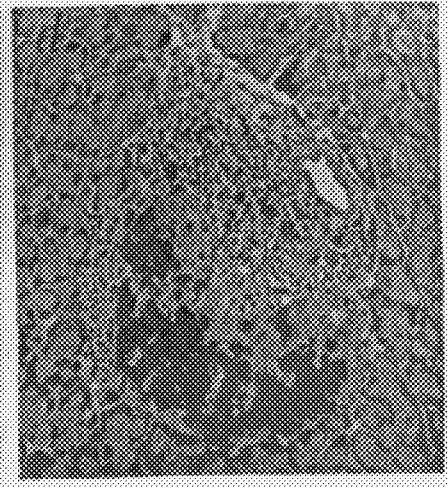
Figure 2E:
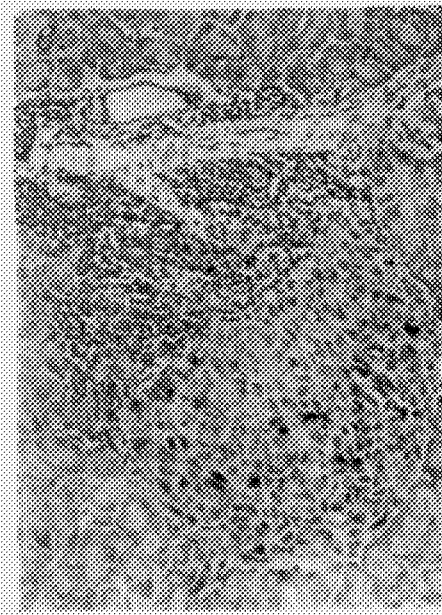
Figure 2F:

In the glucose tolerant group, 4 of 14 control mice did have visible β cells (FIG. 2C). Linomide-treated glucose tolerant mice did not show significantly better results: only 3 of 11 mice had β cells (FIG. 2E). Even relatively few reg protein-treated glucose tolerant mice had β cells, with only 3 of 9 animals showing β cells (FIG. 2D). However, the combination of reg protein and Linomide clearly increased the proportion of mice with visible β cells to 50% (FIG. 2F). Furthermore, as shown in FIG. 2F, islet architecture was relatively maintained with a peri-insulitis pattern.

The ranges of the ratio of β cell mass to total pancreatic cell mass (β cell/total pancreas), as well as of the ratio of β cell mass to islet cell mass (β cell/islet), are as follows for all four groups of glucose tolerant mice. First, the β celutotal pancreas ratio for control mice ranged from 0.0001 to 0.007, while the β cell/islet ratio for control mice ranged from 0 to 0.7. Second, the β cell/total pancreas ratio for reg alone mice ranged from 0.0009 to 0.005, while the β cell/islet ratio for reg alone mice ranged from 0 to 0.6. Third, the β cell/total pancreas ratio for Linomide alone mice ranged from 0.0004 to 0.006, while the β cell/islet ratio for Linomide alone mice ranged from 0 to 0.6. Finally, the β cell/total pancreas ratio for reg+Linomide mice ranged from 0.0002 to 0.007, while the β cell/islet ratio for reg+Linomide mice ranged from 0 to 0.8.

From these results, the ratio of β cell mass to total pancreatic cell mass is not significantly different between the four groups. However, the proportion of β cells within the islets is significantly higher for the group treated with reg and Linomide as compared to the control (p<0.05). Thus, clearly the combination of reg and Linomide preserved β cell mass in glucose tolerant mice. Furthermore, the composition of the present invention was also able to increase the number of animals with visible β cells.

From these results, as well as those shown in Example 1, clearly the combination of an immunoregulator, Linomide, and a β cell proliferation agent, reg protein, was able to significantly reverse the progression of diabetes in glucose intolerant mice, and to visibly preserve β cell mass in glucose tolerant mice, which had relatively less severe disease. Furthermore, even mice which had lost such a significant proportion of β cells as to show overt, frank diabetes were actually able to benefit from this combination, with an accompanying amelioration or complete reversal of the clinical symptoms. Such an effect is of paramount importance for the treatment of human patients with IDDM, since the appearance of clinical symptoms in humans accompanies the destruction of a majority of the β cells in the pancreas. For a treatment for IDDM to be effective, the course of the disease must therefore not only be stopped, but actually reversed, in order to achieve a reduction in the level and frequency of clinical symptoms such as hyperglycemia.

The composition of the present invention, a combination of an immunoregulator and a β cell proliferative agent, fulfills this stringent requirement. Such a requirement is particularly difficult since mature β cells do not normally proliferate, as noted above. For a reversal of the disease state, the process of the autoimmune reaction must be stopped, and the normal inhibition against proliferation of mature β cells must be lifted. Furthermore, the β cells which had been involved in the pathological process of diabetes mellitus must also be able to recover sufficiently to both proliferate and to produce enough insulin to reduce or reverse clinical symptoms of the disease. Thus, the ability of the composition of the present invention to achieve both effects, and then to actually reverse the course of diabetes, is unexpected, and was neither taught nor suggested by the prior art.

EXAMPLE 3

Suitable Formulations for Administration of the Composition

The composition of the present invention, a combination of an immunoregulator and a β cell proliferative agent, can be administered to a subject in a number of ways, which are well known in the art. For example, administration may be done topically (including ophtalmically, vaginally, rectally, intranasally), orally, or parenterally, for example by intravenous drip or intraperitoneal, subcutaneous, or intramuscular injection. If the β cell proliferative agent is a protein such as reg, administration is preferably done parenterally.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

Dosing is dependent on the severity of the symptoms and on the responsiveness of the subject to the composition of the present invention. Persons of ordinary skill in the art can easily determine optimum dosages, dosing methodologies and repetition rates.

EXAMPLE 4

Method of Treatment of Diabetes

As noted above, the composition of the present invention, a combination of an immunoregulator and a β cell proliferative agent, has been shown to be an effective treatment for diabetes. The following example is an illustration only of a method of treating diabetes with the composition of the present invention, and is not intended to be limiting.

The method includes the step of administering the composition of the present invention, in a pharmaceutically acceptable carrier as described in Example 3 above, to a subject to be treated. The composition is administered according to an effective dosing methodology, preferably until a predefined endpoint is reached, such as the absence of further progression of diabetes in the subject, the amelioration of clinical symptoms, the reversal of the progression of diabetes or the prevention of the appearance of clinical symptoms.

EXAMPLE 5

Method of Manufacture of a Medicament

The following is an example of a method of manufacturing a medicament containing the composition of the present invention. First, both the immunoregulator and the β cell proliferative agent are synthesized in accordance with good pharmaceutical manufacturing practice. Examples of such methods are well known in the art. Next, the immunoregulator and the β cell proliferative agent are placed in a suitable pharmaceutical carrier, as described in Example 3 above, again in accordance with good pharmaceutical manufacturing practice.

It will be appreciated that the above descriptions are intended only to serve as examples, and that many other embodiments are possible within the spirit and the scope of the present invention.

What is claimed is:

1. A composition for administration to a glucose intolerant subject for the treatment of diabetes, comprising:
    (a) quinoline-3-carboxamide and pharmaceutically acceptable salts thereof; and
    (b) reg protein;
    said quinoline-3-carboxamide and said reg protein each being in an amount such that a combination of said quinoline-3-carboxamide and said reg protein together has a combined effect greater than an additive effect of each of said quinoline-3-carboxamide and said reg protein separately.

2. A method for treating diabetes in a subject, comprising the step of administering an effective amount of a composition to the subject, the subject being glucose intolerant substantially before said composition is administered to the subject said composition including quinoline-3-carboxamide and pharmaceutically acceptable salts thereof and reg protein in a pharmaceutically acceptable carrier, said quinoline-3-carboxamide and said reg protein each being in an amount such that a combination of said quinoline-3-carboxamide and said reg protein together has a combined effect greater than an additive effect of each of said quinoline-3-carboxamide and said reg protein separately.

3. The method of claim 2, wherein a progression of diabetes in the subject is substantially prevented by administration of said composition.

* * * * *